United States Patent [19]

Xu et al.

[11] Patent Number: 6,011,171

[45] Date of Patent: *Jan. 4, 2000

[54] PROCESS FOR SYNTHESIS OF TERTIARY CARBOXYLIC ACIDS AND THE ESTERS THEREOF

[75] Inventors: Qiang Xu, Suita; Yoshie Souma, Ibaraki, both of Japan

[73] Assignee: Jiro Hiraishi, Director-General, Agency of Industrial Science and Technology, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/964,319

[22] Filed: Nov. 4, 1997

Related U.S. Application Data

[63] Continuation-in-part of application No. 08/910,900, Aug. 13, 1997, abandoned.

[30] Foreign Application Priority Data

Aug. 14, 1996 [JP] Japan ................................... 8-233603
Feb. 25, 1997 [JP] Japan ................................... 9-58425
Jun. 20, 1997 [JP] Japan ................................... 9-180688

[51] Int. Cl.⁷ ................................................. C07C 67/38
[52] U.S. Cl. .................... 560/233; 560/114; 560/204; 560/232; 562/497; 562/519; 562/522
[58] Field of Search .................................. 560/233, 114, 560/204, 232; 562/497, 519, 522

[56] References Cited

U.S. PATENT DOCUMENTS

| | | | |
|---|---|---|---|
| 3,910,963 | 10/1975 | Souma | 560/233 |
| 4,414,409 | 11/1983 | Waller | 560/233 |
| 4,694,100 | 9/1987 | Shimizu | 560/233 |

*Primary Examiner*—Michael L. Shippen
*Attorney, Agent, or Firm*—Nikaido, Marmelstein, Murray & Oram LLP

[57] ABSTRACT

The present invention provides a process for synthesizing tertiary carboxylic acids or the esters thereof having one or two more carbon atoms than the raw material has, comprising reacting in a strong acid (e.g., sulfuric acid, sulfuric acid-phosphoric acid, hydrogen fluoride, fluorosulfuric acid, boron trifluoride.water complex and trifluoromethanesulfonic acid) a raw material compound (i.e., olefin, alcohol, diene, diol or saturated hydrocarbon) with carbon monoxide in the presence of a specific metal carbonyl catalyst (i.e., platinum carbonyl catalyst, palladium carbonyl catalyst and gold dicarbonyl catalyst).

The metal carbonyl catalyst is formed by reacting in a strong acid at least one specific metal compounds (e.g., platinum compound such as platinum (II, IV) oxide, platinum (II, IV) hydroxide, a platinum powder, etc.; palladium compound such as palladium (II, III, IV) oxide, palladium (II) hydroxide, palladium (II) sulfate, palladium (II) carboxylate, a palladium powder, etc.; and gold compound such as gold (I, III) oxide, gold (I, III) hydroxide, a gold powder, etc.) with carbon monoxide.

4 Claims, No Drawings

PROCESS FOR SYNTHESIS OF TERTIARY CARBOXYLIC ACIDS AND THE ESTERS THEREOF

This is a continuation-in-part application of Ser. No. 08/910,900, filed on Aug. 13, 1997, now abandoned.

FIELD OF THE INVENTION

The present invention relates to a process for synthesizing tertiary carboxylic acids and the esters thereof, more specifically to a process for preparing tertiary carboxylic acids and the esters thereof having one more carbon atom than the raw material has, and a process for preparing tertiary dicarboxylic acids and the esters thereof having two more carbon atoms than the raw material has, each process being carried out by reacting the raw material with carbon monoxide.

PRIOR ART

Tertiary carboxylic acids are generally synthesized by a reaction between pressurized carbon monoxide and an olefin in a strong acid. The process is carried out under severe reaction conditions of high temperatures and high pressures and has problems of inducing polymerization of the raw material, which results in the carboxylation of dimers or trimers of raw materials and the formation of secondary carboxylic acids as by-products. Thus, the process is low in selectivity of tertiary carboxylic acids having one more carbon atom than the raw material has.

Derivatives of tertiary carboxylic acids are receiving attention for the usage as materials for preparing a high-quality coating composition, a high-quality surfactant or the like. The derivatives, having two alkyl substituents at the α-position of carbonyl group, are not susceptible to hydrolysis and therefore are excellent in acid resistance, heat resistance and weathering resistance.

However, if the product contains secondary carboxylic acid even in a small amount, acid resistance, heat resistance and weathering resistance are seriously impaired because secondary carboxylic acid is one order of magnitude lower in hydrolytic resistance than tertiary carboxylic acid.

OBJECT OF THE INVENTION

It is a main object of the present invention to provide a process for selectively synthesizing under a milder condition a tertiary carboxylic acid or acid ester which has one more carbon atom than the raw material has, and a process for selectively synthesizing under a milder condition a tertiary dicarboxylic acid or acid ester which has two more carbon atoms than the raw material has.

SUMMARY OF THE INVENTION

The inventors conducted extensive researches and experiments to develop a novel process for selectively synthesizing tertiary carboxylic acids or the esters thereof under mild conditions which will solve or alleviate the above problems of prior art, and found that when the reaction between olefin or the like as the raw material and carbon monoxide in a strong acid for the synthesis of tertiary carboxylic acids is carried out in the presence of a specific metal carbonyl catalyst, tertiary carboxylic acid having one more carbon atom than the raw material has can selectively be synthesized in a high yield even under the conditions of ambient temperature and ambient pressure.

The present invention provides following processes for synthesizing tertiary carboxylic acids or the esters thereof:

1. A process for the synthesis of tertiary carboxylic acids or the esters thereof in which at least one compound selected from the group consisting of olefins, alcohols, dienes, diols and saturated hydrocarbons react(s) with carbon monoxide in the presence of at least one metal carbonyl catalyst selected from the group consisting of platinum carbonyl catalyst, palladium carbonyl catalyst and gold dicarbonyl catalyst in a strong acid.

2. A process for the synthesis of tertiary carboxylic acids or the esters thereof according to Item 1 above, wherein the metal carbonyl catalyst is platinum carbonyl catalyst which is formed by reacting in a strong acid at least one platinum compound selected from the group consisting of platinum (II) oxide, platinum (IV) oxide, platinum (II) hydroxide, platinum (IV) hydroxide and platinum powder with carbon monoxide.

3. A process for the synthesis of tertiary carboxylic acids or the esters thereof according to Item 1 above, wherein the metal carbonyl catalyst is palladium carbonyl catalyst which is formed by reacting in a strong acid at least one palladium compound selected from the group consisting of palladium (II) oxide, palladium (III) oxide, palladium (IV) oxide, palladium (II) hydroxide, palladium (IV) hydroxide, palladium (II) sulfate, palladium (II) carboxylates and palladium powder with carbon monoxide.

4. A process for the synthesis of tertiary carboxylic acids or the esters thereof according to Item 1 above, wherein the metal carbonyl catalyst is gold dicarbonyl catalyst which is formed by reacting at least one gold compound selected from the group consisting of gold (I) oxide, gold (III) oxide, gold (I) hydroxide, gold (III) hydroxide and gold powder with carbon monoxide.

5. A process for the synthesis of tertiary carboxylic acids or the esters thereof according to Item 1 above, wherein the strong acid is at least one species selected from the group consisting of sulfuric acid, a mixture of sulfuric acid-phosphoric acid, hydrogen fluoride, fluorosulfuric acid, boron trifluoride-water complex and trifluoromethane-sulfonic acid.

DETAILED DESCRIPTION OF THE INVENTION

[Metal Carbonyl Catalysts]

In the process of the present invention, a specific metal carbonyl catalyst is used for synthesizing tertiary carboxylic acids or the esters thereof, serving to cause carbonylation reaction of the raw material.

In the present invention, platinum carbonyl catalyst, palladium carbonyl catalyst or gold dicarbonyl catalyst is used as the metal carbonyl catalyst. Platinum carbonyl catalyst and palladium carbonyl catalyst are preferably-used in the embodiments of the invention. Since the compounds of platinum, palladium and gold are not easily oxidized, the metal carbonyl catalysts used in the invention can exhibit highly catalytic activity even in the coexistence of oxygen.

Metal carbonyl catalysts can be produced by causing absorption of carbon monoxide by specific metal compounds (e.g., oxides, hydroxides, metal powders, sulfates and carboxylates).

Suitable examples of the metal compounds for use in the invention are platinum compounds such as platinum (II) oxide, platinum (IV) oxide, platinum (II) hydroxide, platinum (IV) hydroxide, platinum powder, etc.; palladium compounds such as palladium (II) oxide, palladium (III) oxide, palladium (IV) oxide, palladium (II) hydroxide, palladium (IV) hydroxide, palladium (II) sulfate, palladium (II) carboxylates (e.g., palladium acetate (II)), palladium powder, etc.; and gold compounds such as gold (I) oxide, gold (III) oxide, gold (I) hydroxide, gold (III) hydroxide, gold powder, etc.

Metal carbonyl catalysts can be prepared by contacting specified metal compounds with carbon monoxide in a strong acid. Preferred strong acids for use in the present invention include, for example, sulfuric acid, sulfuric acid-phosphoric acid mixture, hydrogen fluoride, boron trifluoride-water complex, fluorosulfuric acid, trifluoromethanesulfonic acid, etc.

Those strong acids may be used alone or in combination of two or more. When a powder such as platinum powder, palladium powder, gold powder and the like is used as the metal compound, metal carbonyl catalysts can be formed by the coexistence of oxidizing agents such as sulfur trioxide, etc.

Platinum compounds such as platinum (II) chloride, platinum (IV) chloride, chloroplatinic acid, platinum (IV) iodide, potassium tetrachloroplatinate (II), potassium hexachloroplatinate (IV) and the like; palladium compounds such as palladium (II) chloride, palladium (III) chloride, palladium (IV) chloride, chloropalladic acid, palladium (II) cyanide, potassium tetrachloropalladate (II), potassium pentachloropalladate (III), potassium hexachloropalladate (IV) and the like; and gold compounds such as gold (I) cyanide, sodium cyanoaurate, potassium cyanoaurate, tetrachloroauric (III) acid and the like are readily available from commercial sources, but are less preferred due to their low ability to form metal carbonyl catalysts.

Examples of platinum carbonyl catalysts include platinum carbonyl complexes of the formula $[Pt(CO)_n](HSO_4)_m$ (wherein n=1 to 6 and m=1 to 4). When reaction is conducted using platinum (IV) oxide as the platinum compound and sulfuric acid as the strong acid, platinum carbonyl catalyst is formed as shown in the following chemical equation (1) wherein n represents the number of CO coordinated to platinum (1 to 6) and m represents the number of counter anion per platinum atom (1 to 4).

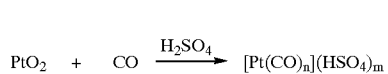

(1)

Examples of palladium carbonyl catalysts include palladium carbonyl complexes of the formula $[Pd_2(CO)_m]^{2+}$ (wherein m=1 to 4) and palladium carbonyl complexes of the formula $[Pd(CO)_n]^{2+}$ (wherein n=1 to 4). When reaction is conducted using palladium (II) oxide as the palladium compound and sulfuric acid as the strong acid, palladium carbonyl catalyst is formed as shown in the following chemical equation (2) wherein m and n represent the number of CO coordinated to palladium (1 to 4).

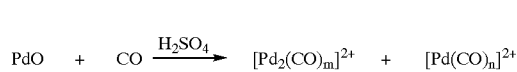

(2)

Examples of gold carbonyl catalysts include gold carbonyl complex of the formula $[Au(CO)_2]^+$. When reaction is conducted using gold (III) oxide as the gold compound and sulfuric acid as the strong acid, gold carbonyl catalyst is formed as shown in the following chemical equation (3). By reacting with carbon monoxide in a strong acid such as sulfuric acid, trivalent gold compound (e.g., gold (III) oxide, gold (III) hydroxide) is reduced by CO to form gold (I) carbonyl catalyst. In the chemical equation (3), gold monocarbonyl $Au(Co)^+$ is catalytically inactive. In the process of the present invention, only gold dicarbonyl $Au(CO)_2^+$ acts as the catalyst.

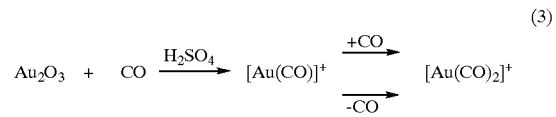

(3)

[Synthesis of Tertiary Carboxylic Acids or the Esters Thereof]

Tertiary carboxylic acid or the ester thereof can be synthesized by adding the raw material compound to a strongly acidic solution containing at least one metal carbonyl catalyst selected from the group consisting of platinum carbonyl catalyst, palladium carbonyl catalyst and gold dicarbonyl catalyst and inducing reaction with carbon monoxide.

Metal carbonyl catalysts may be used alone or in combination of two or more kinds. Other catalysts may also be used in admixture with the above catalysts unless they adversely affect the function of the metal carbonyl catalysts.

Sulfuric acid, sulfuric acid-phosphoric acid mixture, hydrogen fluoride, boron trifluoride-water complex, fluorosulfuric acid, trifluoromethanesulfonic acid and the like may be used alone or in combination of two or more.

The strong acidic solution which contains a specific metal carbonyl catalyst obtained by the reaction of a metal compound (platinum compound, palladium compound or gold compound) with carbon monoxide in a strong acid may be used as it is as the catalyst to synthesize tertiary carboxylic acids or the esters thereof.

Addition of the raw material compound to the strong acidic solution containing a specified metal carbonyl catalyst causes the formation of carbocation. In the strong acidic solution, the carbocation is isomerized to form tertiary carbocations.

When the tertiary carbocation reacts with carbon monoxide in the presence of a specified metal carbonyl catalyst and water is added thereto, a tertiary carboxylic acid is produced. Alternatively, when the tertiary carbocation reacts with carbon monoxide and an alcohol is added thereto, a tertiary carboxylic acid ester is produced.

When an olefin or alcohol used as the raw material is added to the strong acidic solution containing a specific metal carbonyl catalyst, the olefin undergoes proton addition, and the alcohol undergoes proton addition and subsequent dehydration, to give a carbocation.

When the reaction is performed using olefin or alcohol as the raw material, synthesis of tertiary carboxylic acid proceeds as shown, for example, in the following chemical equation (wherein R, R' and R" each represent an alkyl group carried by the raw material of olefin or alcohol, and $R^1$, $R^2$ and $R^3$ each represent an alkyl group carried by the reaction intermediate or the final product).

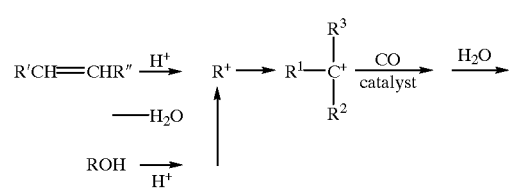

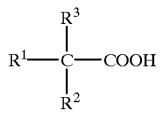

Preferred olefins for use in the present invention are olefins having 4 or more carbon atoms, for example, olefins having 4 to 20 carbon atoms. Any of olefins such as the olefin having a double bond at the end in the molecule, the olefin having a double bond internally in the molecule and cyclic olefin may be used. Suitable examples of olefins include 1-butene, 2-butene, 1-hexene, 2-ethyl-1-hexene, 1-octene, 1-nonene, 1-decene, butene dimer, butene trimer, propylene dimer, propylene trimer, cyclohexene, cyclooctene, etc.

Preferred alcohols for use in the present invention are alcohols having 4 or more carbon atoms, for example, alcohols having 4 to 20 carbon atoms. Primary alcohols, secondary alcohols, tertiary alcohols and cyclic alcohols may be used.

Suitable examples of alcohols include 1-butanol, 2-butanol, 2-methyl-2-propanol, 1-pentanol, 2-pentanol, 3-methyl-3-butanol, 1-hexanol, 2-hexonol, 3-methyl-3-heptanol, 1-heptanol, 2-heptanol, 3-methyl-3-hexanol, 1-octanol, 2-octanol, 2-methyl-1-hexanol, 1-decanol, 2-dodecanol, 1-nonyl alcohol, 1-dodecanol, cyclohexanol, etc.

As the raw material, dienes and diols preferably having 8 or more carbon atoms, especially dienes and diols having 8 to 26 carbon atoms may be used. All dienes having two double bonds in the molecule may be used. All diols having two hydroxyl groups in the molecule may be used.

Dienes or diols having 8 or more carbon atoms can react with carbon monoxide to produce tertiary carboxylic acid or the ester thereof having two additional carbon atoms. Examples of such dienes and diols include 1,7-octadiene, 1,9-decadiene, 1,11-dodecadiene, 1,12-tridecadiene, limonene, 1,10-decanediol, 1,12-dodecanediol, 2,9-dimethyldecanediol and the like.

As the raw material, saturated hydrocarbons preferably having 4 or more carbon atoms, especially those having 4 to 20 carbon atoms may be used. All of the saturated hydrocarbons having tertiary carbon may be used. Examples of such saturated hydrocarbons include methylcyclohexane, methylcyclopentane, ethylcyclohexane, ethylcyclopentane, methylcyclooctane, 2-ethylhexane, 3-ethylhexane, etc.

When saturated hydrocarbon having a tertiary carbon is employed in the presence of the carbocation-producing compound such as olefin, alcohol or the like, a tertiary carboxylic acid can be synthesized.

In more detail, carbocation causes abstraction of the hydrogen on the tertiary carbon of the saturated hydrocarbon and the newly produced carbocation reacts with carbon monoxide to produce a tertiary carboxylic acid. When, for example, methylcyclohexane is used as the saturated hydrocarbon, synthesis of tertiary carboxylic acid proceeds as shown in the following chemical equation.

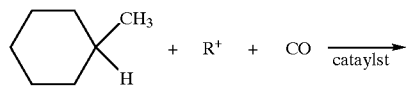

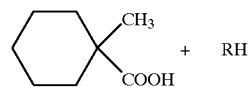

The carbonylation of the raw material compound smoothly proceeds under ambient temperature and pressure. The reaction pressure is not specifically limited, but the pressure from 0.1 to 10 atm is generally used. The pressure from 0.5 to 5 atm is preferable.

In the case where partial pressure of carbon monoxide is low due to the coexistence of other gases such as air, the reaction can be accelerated by pressurizing the reactor. The reaction temperature employed in the invention is not specifically limited, but it generally ranges from about −10° C. to about 60° C., the temperature between 5° C. and 40° C. is the most preferable.

The present invention may be carried out, for example, in the following manner. To a sealable reaction vessel containing a strong acid, the specified metal compounds (platinum compound, palladium compound or gold compound) are added alone or in combination of two or more. Then the vessel is evacuated by means of a vacuum pump, and carbon monoxide is introduced thereto, followed by vigorous stirring. The metal compound dissolves while reacting with carbon monoxide to form a metal carbonyl catalyst.

By adding a raw material such as olefin or alcohol, to the catalyst solution, the reaction between the raw material and carbon monoxide takes place. The addition of the reaction mixture to ice-water or alcohol results in the formation of a tertiary carboxylic acid or the ester thereof. The product can be separated from the reaction mixture by extracting with organic solvent such as hexane or the like.

As for alcohols to produce ester of tertiary carboxylic acid, suitable alcohols include but are not limited to, suitable are any alcohol capable of producing the ester of tertiary carboxylic acid, such as primary alcohols, secondary alcohols, tertiary alcohols and cyclic alcohols.

Illustrative of such alcohols are methanol, ethanol, 1-propanol, 2-propanol, 1-butanol, 2-butanol, 2-methyl-2-propanol, 1-pentanol, 2-pentanol, 3-methyl-3-butanol, 1-hexanol, 2-hexanol, 3-methyl-3-heptanol, 1-heptanol, 2-heptanol, 3-methyl-3-hexanol, 1-octanol, 2-octanol, 2-methyl-1-hexanol, 1-decanol, 2-dodecanol, 1-nonyl alcohol, 1-dodecanol, cyclohexanol, etc.

In the present invention, carbon monoxide coordinated to a specified metal (platinum, palladium or gold) contributes to the reaction. The catalytic activity depends on the coordination number of CO in the metal carbonyl complex. In the case of gold carbonyl catalyst, since only gold dicarbonyl $Au(CO)_2^+$ exhibits catalytic activity, reaction conditions should be controlled so that gold dicarbonyl can be efficiently formed.

A series of carbonylation reactions was performed using 1-hexene as the raw material and sulfuric acid as the strong acid. The results are given in the yield of tertiary $C_7$ carboxylic acid on the amount of gold dicarbonyl with various concentration of $H_2SO_4$.

Relation between gold dicarbonyl formation and tertiary $C_7$ carboxylic acid yield

| Concentration of sulfuric acid (%) | Amount of formed gold dicarbonyl $Au(CO)_2^+/AU^+$ | Tertiary $C_7$ carboxylic acid yield (%) |
| --- | --- | --- |
| 75 | 0 | 0 |
| 80 | 0.07 | 25 |
| 85 | 0.18 | 32 |
| 90 | 0.43 | 58 |
| 93 | 0.58 | 78 |
| 96 | 0.69 | 78 |

The reaction was carried out by using gold (III) hydroxide (1 mmol) to prepare gold dicarbonyl catalyst and 1-hexene (5 mmol) to produce tertiary carboxylic acid at 25° C. and 1 atm. As shown in the table, the usage of concentrated sulfuric acid above 80% is necessary to form gold dicarbonyl. With the increase of $H_2SO_4$ concentration, the amount of gold dicarbonyl increased, then the yield of tertiary $C_7$ carboxylic acid increased proportionally.

EFFECTS OF THE INVENTION

According to the present invention, the carbonylation reaction between olefin or the like and carbon monoxide is highly accelerated. When a specific metal carbonyl catalyst is present in the reaction solution, the concentration of carbon monoxide in the solution can be elevated to a higher level to promote the carbonylation reaction, and as a result, the raw material is prevented from polymerization.

According to the present invention, it is possible to selectively produce tertiary carboxylic acids or the esters thereof which have 1 or 2 more carbon atoms than the raw material in a high yield, even under the conditions of room temperature and atmospheric pressure. Further, the metal carbonyl catalyst used in the present invention is advantageous since its catalytic activity is not impaired even in the presence of air or oxygen.

EXAMPLES
[Platinum Carbonyl Catalyst]

Example 1-1

To a 200 ml volume three-necked flask connected with a gas burette were added platinum (IV) hydroxide (526 mg, 2 mmol) and 96% sulfuric acid (10 ml). After the air in the flask was evacuated by means of a vacuum pump, carbon monoxide was introduced at 25° C. and 1 atm into the flask, followed by vigorous stirring. During the reaction for three days, absorption of 150 ml of carbon monoxide occurred to give a solution containing platinum carbonyl catalyst.

When 1-hexene (0.62 ml, 5 mmol) was slowly added to the solution containing catalyst, 82 ml of carbon monoxide was consumed for carbonylation of 1-hexene over a period of 30 minutes. The resultant reaction mixture was added to ice-water and the product was extracted twice with n-hexane. Analyses by gas chromatography (GC), NMR, IR and GC-MS revealed that a 2:1 mixture of 2,2-dimethylpentanoic acid and 2-methyl-2-ethylbutanoic acid was produced, and the total yield was 73% as determined by titration of 0.1 N NaOH solution.

Example 1-2

To a 200 ml volume three-necked flask connected with a gas burette were added platinum (IV) oxide (454 mg, 2 mmol) and 96% sulfuric acid (10 ml). After the air in the flask was evacuated by means of a vacuum pump, a mixed gas containing 80% carbon monoxide and 20% air was introduced to the flask at 25° C. and 1 atm, followed by vigorous stirring. During the reaction for three days, 150 ml of carbon monoxide was absorbed to form platinum carbonyl catalyst.

When 1-octanol (0.79 ml, 5 mmol) was slowly added to the catalyst solution, 79 ml of carbon monoxide was further absorbed by 1-octanol. The resulting reaction mixture was added to ice-water and the product was extracted with n-hexane. Analyses by GC, NMR, IR and GC-MS indicated that a 4:2:1 mixture of 2,2-dimethylheptanoic acid, 2-methyl-2-ethylhexanoic acid and 2-methyl-2-propylpentanoic acid was produced, and the total yield of the mixture was 71% as determined by titration of a 0.1 N NaOH solution.

Example 1-3

After displacing air by carbon monoxide, a 200 ml volume three-necked flask connected with a gas burette was charged with platinum (II) hydroxide (458 mg, 1 mmol) and hydrogen fluoride (5 ml). Carbon monoxide was absorbed by the platinum with vigorous stirring to give a solution containing platinum carbonyl catalyst. When 1-butene (112 ml, 5 mmol) was introduced through a gas burette into the flask, it reacted with 68 ml of carbon monoxide.

After the reaction, methanol (3 ml) was added to form methylester and unreacted hydrogen fluoride was distilled away. The product was extracted with hexane and subjected to analyses by GC, NMR, IR, etc. The analyses indicated that pivalic acid methylester was produced in a yield of 53%.

Example 1-4

After displacing air by carbon monoxide, a 200 ml volume three-necked flask was charged with platinum (II) oxide (422 mg, 2 mmol) and boron trifluoride-water complex (10 ml). Carbon monoxide was absorbed by platinum with vigorous stirring to form a solution containing platinum carbonyl catalyst. To the catalyst solution was slowly added 1,11-dodecadiene (1.1 ml, 5 mmol) to induce a reaction with carbon monoxide.

The product was extracted with benzene and one fifth of the product was titrated with a 0.1 N NaOH solution. Analyses by NMR and IR indicated that a mixture of tertiary carboxylic acids having 14 carbon atoms containing 2,2,9,9-tetramethyldecanedicarboxylic acid as a main component was produced in a yield of 51%.

Example 1-5

After displacing air by carbon monoxide, a 200 ml volume three-necked flask was charged with platinum (IV) hydroxide (526 mg, 2 mmol), concentrated sulfuric acid (7 ml) and fluorosulfuric acid (3 ml) and the mixture obtained was vigorously stirred to form a platinum carbonyl catalyst. 1,12-dodecanediol (1.12 ml, 5 mmol) was added to the resultant reaction mixture to allow a further reaction with carbon monoxide.

The product obtained was extracted with benzene and one fifth of the product was titrated with a 0.1 N NaOH solution. Analyses by NMR and IR showed that a mixture of tertiary carboxylic acids having 14 carbon atoms which contained 2,2,9,9-tetramethyldecane-dicarboxylic acid as a main component was produced in a yield of 60%.

Example 1-6

Employing platinum (IV) hydroxide (526 mg) and 96% sulfuric acid (10 ml), a solution containing platinum carbonyl catalyst was prepared in a similar manner to Example 1-1. To the solution containing catalyst was slowly added a mixture of methylcyclohexane (0.64 ml) and 1-hexene (0.62 ml) to cause a further reaction with carbon monoxide.

The resultant reaction mixture was added to ice-water and the product was extracted with n-hexene. GC, NMR, IR and GC-MS analyses indicated that a 3:1 mixture of methylcyclohexanecarboxylic acid and tertiary carboxylic acids having 7 carbon atoms was produced, and the yield of methylcyclohexanecarboxylic acid was 59% as determined by titration with a 0.1 N NaOH solution.

Example 1-7

Into a 200 ml volume three-necked flask connected with a gas burette were placed platinum powder (195 mg) and sulfuric acid (10 ml). After displacement of the air in the flask by carbon monoxide, sulfur trioxide (4.5 g) was added to give a solution containing platinum carbonyl catalyst.

To the catalyst solution, octane (0.81 ml, 5 mmol) was slowly added to allow a further reaction with carbon monoxide. The reaction mixture was added to ice-water and the product formed was extracted with n-hexane. Analyses by GC, NMR and IR revealed that 2,2-dimethylpropanoic acid was produced, and the yield was 140 mole % based on the amount of octane as determined by titration with a 0.1 N NaOH solution.

Example 1-8

To sulfuric acid (10 ml) was added, respectively, each of platinum compounds in the amount shown in Table 1 below. Air in the flask (atmosphere) was displaced with carbon monoxide at 1 atm and vigorous stirring was provided to form platinum carbonyl catalyst. Then 1-hexene (5 ml) was slowly added to the catalyst solution at 25° C. to induce the reaction with carbon monoxide and produce tertiary carboxylic acid having 7 carbon atoms. Yields of the obtained tertiary carboxylic acid having 7 carbon atoms are shown in Table 1.

TABLE 1

| Platinum compound | Amount added | Yield of tertiary carboxylic acid |
| --- | --- | --- |
| Not added | | 15% |
| $PtO_2$ | 2 mmol | 73% |
| PtO | 2 mmol | 72% |
| $Pt(OH)_2$ | 2 mmol | 72% |
| Pt (platinum powder) | 2 mmol | 70% |

As shown in Table 1, the absence of platinum compound in the reaction system results in a low yield of carboxylic acid, whereas the use of platinum compound in the system considerably accelerates carbonylation reaction, providing an extremely high yield of tertiary carboxylic acid.

[Palladium Carbonyl Catalyst]

Example 2-1

Into a 200 ml volume three-necked flask connected with a gas burette were placed palladium (II) oxide (245 mg, 2 mmol) and 96% sulfuric acid (10 ml). After evacuating the air in the flask by means of a vacuum pump, carbon monoxide was introduced into the flask at 25° C. and 1 atm, followed by vigorous stirring. 45 ml of carbon monoxide was absorbed by palladium oxide to give a solution containing palladium carbonyl catalyst.

When 1-hexene (0.62 ml, 5 mmol) was slowly added to the catalyst solution, 82 ml of carbon monoxide was consumed over a period of 30 minutes. The reaction mixture was added to ice-water and the product was extracted twice with n-hexane. Analyses by GC, NMR, IR and GC-MS revealed that a 2:1 mixture of 2,2-dimethylpentanoic acid and 2-methyl-2-ethylbutanoic acid was produced, and the total yield of the mixture was 68% as determined by titration of a 0.1 N NaOH solution.

Example 2-2

Into a 200 ml volume three-necked flask connected to a gas burette were placed palladium (IV) oxide (277 mg, 2 mmol) and 96% sulfuric acid (10 ml). After evacuating the air in the flask by means of a vacuum pump, a mixed gas containing 80% carbon monoxide and 20% air was introduced into the flask at 25° C. and 1 atm, followed by vigorous stirring. 45 ml of carbon monoxide was absorbed by palladium oxide to form a palladium carbonyl catalyst.

When 1-octanol (0.79 ml, 5 mmol) was slowly added to the catalyst solution, 79 ml of carbon monoxide was additionally absorbed. The reaction mixture was then added to ice-water and the product was extracted with n-hexane. Analyses by GC, NMR, IR and GC-MS revealed that a 4:2:1 mixture of 2,2-dimethylheptanoic acid, 2-methyl-2-ethylhexanoic acid and 2-methyl-2-propylpentanoic acid was produced. The total yield of the mixture was found to be 75% as determined by titration of a 0.1 N NaOH solution.

Example 2-3

After displacement of air by carbon monoxide, a 200 ml volume three-necked flask connected to a gas burette was charged with palladium (II) sulfate (405 mg, 1 mmol) and hydrogen fluoride (5 ml). The mixture was vigorously stirred to cause absorption of carbon monoxide, whereby a solution containing palladium carbonyl catalyst was obtained.

When 1-butene (112 ml, 5 mmol) was introduced to the catalyst solution, 68 ml of carbon monoxide was absorbed. After the reaction, methanol (3 ml) was added to give methylester and then the unreacted hydrogen fluoride was distilled away. The product was extracted with hexane and analyzed by GC, NMR, IR, etc. The analyses demonstrated that pivalic acid methylester was produced in 51% yield.

Example 2-4

After displacement of air by carbon monoxide, a 200 ml volume three-necked flask was charged with palladium (II) hydroxide (281 mg, 2 mmol) and boron trifluoride-water complex (10 ml) and the mixture was vigorously stirred to give a solution containing palladium carbonyl catalyst with absorption of carbon monoxide.

To the solution was slowly added 1,11-dodecadiene (1.1 ml, 5 mmol) to induce reaction with carbon monoxide. The product was extracted with benzene and one fifth of the product was titrated with a 0.1 N NaOH solution. Analyses by NMR and IR indicated that tertiary carboxylic acids having 14 carbon atoms which contained 2,2,9,9-tetramethyldecanedicarboxylic acid as a main component was produced in 53% yield.

Example 2-5

After displacing air by carbon monoxide, a 200 ml volume three-necked flask was charged with palladium (II) sulfate (405 mg, 2 mmol), concentrated sulfuric acid (7 ml) and fluorosulfuric acid (3 ml) and the mixture was vigorously stirred to give palladium carbonyl catalyst. 1,12-dodecanediol (1.12 ml, 5 mmol) was added to cause reaction with carbon monoxide.

The product was extracted with benzene and one fifth of the product was titrated with a 0.1 N NaOH solution. The titration and analyses by NMR and IR showed that tertiary carboxylic acids having 14 carbon atoms and containing 2,2,9,9-tetramethyldecane-dicarboxylic acid as a main constituent was produced in 60% yield.

Example 2-6

Using palladium (II) oxide (245 mg) and 96% sulfuric acid (10 ml), a solution containing palladium carbonyl catalyst was prepared in a similar manner to Example 2-1. To the solution containing catalyst produced was slowly added a mixture of methylcyclohexane (0.64 ml) and 1-hexene (0.62 ml) to cause reaction with carbon monoxide.

The reaction mixture was added to ice-water and the product obtained was extracted with n-hexane. GC, NMR, IR and GC-MS analyses indicated that a 3:1 mixture of methylcyclohexanecarboxylic acid and tertiary carboxylic acids having 7 carbon atoms was produced. The yield of methylcyclohexanecarboxylic acid was 55% as determined by titration with a 0.1 N NaOH solution.

Example 2-7

Into a 200 ml volume three-necked flask connected with a gas burette were introduced palladium powder (213 mg) and sulfuric acid (10 ml), After displacement of the air in the flask with carbon monoxide, sulfur trioxide (4.5 g) was added to give a solution containing palladium carbonyl catalyst. To the catalyst solution, octane (0.81 ml, 5 mmol) was slowly added to allow reaction with carbon monoxide.

The reaction mixture was then added to ice-water and the product was extracted with n-hexane. Analyses by GC, NMR and IR revealed that 2,2-dimethylpropanoic acid was produced, and the yield of the product was 125 mole % based on the amount of octane as determined by titration with a 0.1 N NaOH solution.

Example 2-8

To sulfuric acid (10 ml) was added each of palladium compounds in the amount shown in Table 2. Air in the flask (atmosphere) was displaced with carbon monoxide (1 atm) and the liquid phase was vigorously stirred to form a palladium carbonyl catalyst. Then 1-hexene (5 ml) was slowly added at 25° C. to the resultant catalyst solution to induce the reaction with carbon monoxide and produce tertiary carboxylic acids having 7 carbon atoms. Yields of the obtained tertiary carboxylic acids having 7 carbon atoms are shown in Table 2.

TABLE 2

| Palladium compound | Amount added | Yield of tertiary carboxylic acid |
| --- | --- | --- |
| Not added | | 15% |
| PdO | 2 mmol | 68% |
| $PdO_2$ | 2 mmol | 68% |
| $PdSO_4$ | 2 mmol | 70% |
| $Pd(OH)_2$ | 2 mmol | 67% |
| $Pd(CH_3COO)_2$ | 2 mmol | 69% |
| Pd (palladium powder) | 2 mmol | 65% |

As shown in Table 2, the absence of palladium compound in the reaction system results in a low yield of carboxylic acids, whereas the presence of palladium compound in the system considerably promotes carbonylation reaction, affording a very high yield of tertiary carboxylic acids.

[Gold Carbonyl Catalyst]

Example 3-1

To a 300 ml volume three-necked flask connected to a gas burette were added gold (III) hydroxide (248 mg, 1 mmol) and 96% sulfuric acid (10 ml). After the evacuation of air from the flask by means of a vacuum pump, carbon monoxide was introduced into the flask at 25° C. and 1 atm, followed by vigorous stirring of the contents. During the reaction for 20 minutes, 38 ml of carbon monoxide was absorbed to give a clear solution containing gold carbonyl catalyst.

When 1-hexene (0.62 ml, 5 mmol) was slowly added to the catalyst solution, 90 ml of carbon monoxide was consumed during a reaction for 30 minutes. The reaction mixture was added to ice-water and the product was extracted with n-hexane twice. Analyses by GC, NMR, IR and GC-MS revealed that a 2:1 mixture of 2,2-dimethylpentanoic acid and 2-methyl-2-ethylbutanoic acid was produced, and the total yield of the product was 80% as determined by titration with a 0.1 N NaOH solution.

Example 3-2

To a 300 ml volume three-necked flask connected with a gas burette were added gold (III) oxide (271 mg, 0.5 mmol) and 96% sulfuric acid (10 ml). After evacuating air from the flask by means of a vacuum pump, a mixed gas containing 80% carbon monoxide and 20% air was introduced at 25° C. and 1 atm, followed by vigorous stirring of the flask content. After 20 minutes, 38 ml of carbon monoxide was found to have been absorbed by the gold (III) oxide to produce a clear solution containing gold carbonyl catalyst.

When 1-octanol (0.79 ml, 5 mmol) was slowly added to the solution containing catalyst, 88 ml of carbon monoxide was absorbed during a 30-minute reaction. The reaction mixture was then added to ice-water and the product formed was extracted with n-hexane.

The purified product was analyzed by GC, NMR, IR and GC-MS and was found to be a 4:2:1 mixture of 2,2-dimethylheptanoic acid, 2-methyl-2-ethylhexanoic acid and 2-methyl-2-propylpentanoic acid. The total yield of the product was 78% as determined by the titration of a 0.1 N NaOH solution.

Example 3-3

After displacement of air by carbon monoxide, a 300 ml volume three-necked flask connected to a gas burette was charged with gold (I) hydroxide (214 mg, 1 mmol) and hydrogen fluoride (5 ml). The mixture was subjected to vigorous stirring, causing absorption of carbon monoxide to form gold carbonyl catalyst. 1-butene (112 ml, 5 mmol) was introduced to the flask to initiate the reaction with 73 ml of carbon monoxide.

After completion of the reaction, methanol (3 ml) was added to the resultant reaction mixture to form methylester and the unreacted hydrogen fluoride was distilled off. The product was extracted with hexane and analyzed by GC, NMR and IR. The analyses demonstrated that pivalic acid methylester was produced in 55% yield.

Example 3-4

After displacing air by carbon monoxide, a 300 ml volume three-necked flask was charged with gold (III) hydroxide (248 mg, 1 mmol) and boron trifluoride-water complex (5 ml). The mixture absorbed carbon monoxide when subjected to vigorous stirring, forming gold carbonyl catalyst. To the catalyst solution was slowly added 1,11-dodecadiene (1.1 ml, 5 mmol) to induce reaction with carbon monoxide.

The resulting reaction product was extracted with benzene and one fifth of the product was titrated with a 0.1 N NaOH solution. Analyses by NMR and IR indicated that tertiary carboxylic acids having 14 carbon atoms containing 2,2,9,9-tetramethyldecanedicarboxylic acid as a main component was produced. The yield was 52%.

Example 3-5

After displacement of air by carbon monoxide, a 200 ml volume three-necked flask was charged with gold (III) hydroxide (496 mg, 2 mmol) and fluorosulfuric acid (3 ml). The mixture was vigorously stirred to form gold carbonyl catalyst. 1,12-dodecanediol (1.12 ml, 5 mmol) was added to the reaction mixture to allow reaction with carbon monoxide.

The product formed was extracted with benzene and one fifth of the product was titrated with a 0.1 N NaOH solution. Analyses by NMR and IR showed that tertiary carboxylic acids having 14 carbon atoms containing 2,2,9,9-tetramethyldecanedicarboxylic acid as a main component was produced. The yield was 59%.

Example 3-6

Using gold (III) hydroxide (248 mg, 1 mmol) and 96% sulfuric acid (10 ml), gold carbonyl catalyst was prepared in a similar manner to Example 3-1. To the solution containing catalyst was slowly added a mixture of methylcyclohexane (0.64 ml) and 1-hexene (0.62 ml) to cause reaction with carbon monoxide.

The resultant reaction mixture was added to ice-water and the product was extracted with n-hexane. GC, NMR, IR and GC-MS analyses indicated that a 3:1 mixture of methylcyclohexane-carboxylic acid and tertiary carboxylic acids having 7 carbon atoms was produced. The yield of methylcyclohexanecarboxylic acid was 60% as determined by titration with a 0.1 N NaOH solution.

Example 3-7

To a 300 ml volume three-necked flask connected with a gas burette were added gold powder (197 mg) and sulfuric acid (10 ml). After displacing the air in the flask with carbon monoxide, sulfur trioxide (4.5 mg) was added to the mixture to form gold carbonyl catalyst.

To the catalyst solution, octane (0.81 ml, 5 mmol) was slowly added to cause reaction with carbon monoxide. The reaction mixture was added to ice-water and the product was extracted with n-hexane. Analyses by GC, NMR and IR revealed that 2,2-dimethylpropanoic acid was produced. The yield was 160 mole % based on the amount of octane as determined by titration with a 0.1 N NaOH solution.

Example 3-8

To sulfuric acid (10 ml) was added a gold compound in the amount shown in Table 3. After air in the flask was displaced with carbon monoxide of 1 atm, the mixture was vigorously stirred to form gold carbonyl catalyst. Then 1-hexene (5 mmol) was slowly added to the catalyst solution at 25° C. to induce the reaction and produce tertiary carboxylic acid having 7 carbon atoms. Yields of the obtained tertiary carboxylic acid having 7 carbon atoms are shown in Table 3.

TABLE 3

| Gold compound | Amount added | Yield of tertiary carboxylic acid |
|---|---|---|
| Not added | | 15% |
| $Au_2O_3$ | 0.5 mmol | 80% |
| $Au_2O_3$ | 1 mmol | 79% |
| Au(OH) | 1 mmol | 80% |
| $Au(OH)_3$ | 1 mmol | 78% |
| Au(gold powder) | 1 mmol | 70% |

As seen from the results shown in Table 3, the absence of gold compound in the reaction system results in a low yield of carboxylic acid, whereas the presence of gold compound in the system accelerates carbonylation reaction, affording a high yield of tertiary carboxylic acid.

Example 3-9

To sulfuric acid (10 ml) of various concentrations shown in Table 4 was added gold (III) hydroxide (1 mmol). After air in the flask was displaced with carbon monoxide of 1 atm, the mixture was subjected to vigorous stirring to form gold carbonyl catalyst.

Then 1-hexene (5 mmol) was slowly added to the reaction mixture at 25° C. to induce the reaction with carbon monoxide and produce tertiary carboxylic acid having 7 carbon atoms. The molar ratio of carbon monoxide to gold in gold carbonyl catalyst (CO/Au) and the yield of the obtained tertiary carboxylic acid having 9 carbon atoms are shown in Table 4.

TABLE 4

| Concentration of sulfuric acid (%) | Gold carbonyl catalyst CO/Au | Tertiary carboxylic acid Yield (%) |
|---|---|---|
| 75 | 1.00 | 0 (Comparative Ex.) |
| 80 | 1.07 | 25 |
| 85 | 1.18 | 32 |
| 90 | 1.43 | 58 |
| 93 | 1.58 | 78 |
| 96 | 1.69 | 78 |

We claim:

1. A process for the synthesis of tertiary carboxylic acids or the esters thereof in which at least one compound selected from the group consisting of olefins, alcohols, dienes, diols and saturated hydrocarbons react(s) with carbon monoxide in the presence of at least one metal carbonyl catalyst selected from the group consisting of platinum carbonyl catalyst and palladium carbonyl catalyst in a strong acid, at a pressure of 0.1 to 10 atm, and at a temperature of 5° C. to 40° C., and at least one of water and alcohols is added thereto.

2. A process for the synthesis of tertiary carboxylic acids or the esters thereof according to claim 1 wherein the metal carbonyl catalyst is platinum carbonyl catalyst which is formed by reacting in a strong acid at least one platinum compound selected from the group consisting of platinum (II) oxide, platinum (IV) oxide, platinum (II) hydroxide, platinum (IV) hydroxide and platinum powder with carbon monoxide.

3. A process for the synthesis of tertiary carboxylic acids or the esters thereof according to claim 1 wherein the metal carbonyl catalyst is palladium carbonyl catalyst which is formed by reacting in a strong acid at least one palladium compound selected from the group consisting of palladium (II) oxide, palladium (III) oxide, palladium (IV) oxide, palladium (II) hydroxide, palladium (II) sulfate, palladium (II) carboxylate and palladium powder with carbon monoxide.

4. A process for the synthesis of tertiary carboxylic acids or the esters thereof according to claim 1 wherein the strong acid is at least one species selected from the group consisting of sulfuric acid, a mixture of sulfuric acid-phosphoric acid, hydrogen fluoride, fluorosulfuric acid, boron trifluoride-water complex and trifluoromethane-sulfonic acid.

\* \* \* \* \*